United States Patent [19]
Buizer et al.

[11] Patent Number: 5,914,263
[45] Date of Patent: Jun. 22, 1999

[54] ENZYMATIC PROCESS FOR THE STEREOSELECTIVE PREPARATION OF A HETERO-BICYCLIC ALCOHOL ENANTIOMER

[75] Inventors: Nicolaas Buizer; Chris G. Kruse; Melle Van Der Laan, all of Weesp, Netherlands; Georges Langrand, Nice, France; Gustaaf J.M. Van Scharrenburg; Maria C. Snoek, both of Weesp, Netherlands

[73] Assignee: Duphar International Research B.V., Weesp, Netherlands

[21] Appl. No.: 08/899,155

[22] Filed: Jul. 23, 1997

Related U.S. Application Data

[62] Division of application No. 08/167,084, Dec. 16, 1993.

[30] Foreign Application Priority Data

Dec. 21, 1992 [EP] European Pat. Off. .............. 92204043

[51] Int. Cl.$^6$ ..................................................... C12P 41/00
[52] U.S. Cl. ......................... 435/280; 435/155; 435/156; 435/120; 435/125
[58] Field of Search .................................. 435/280, 155, 435/156, 117, 120, 123, 125

[56] References Cited

U.S. PATENT DOCUMENTS

| | | | |
|---|---|---|---|
| 3,692,775 | 9/1972 | Kubanek et al. | 540/486 |
| 3,887,606 | 6/1975 | Phillipps et al. | 560/38 |
| 4,539,413 | 9/1985 | Mouzin et al. . | |
| 4,540,792 | 9/1985 | Commeyras et al. . | |
| 4,659,671 | 4/1987 | Klibanov | 435/280 |
| 4,762,793 | 8/1988 | Cesti et al. | 435/280 |
| 4,833,142 | 5/1989 | Hartog et al. . | |
| 4,889,852 | 12/1989 | Hartog et al. . | |
| 5,166,062 | 11/1992 | Morrow et al. | 435/280 |

FOREIGN PATENT DOCUMENTS

| | | |
|---|---|---|
| 0089886 | 9/1983 | European Pat. Off. . |
| 0185429 | 6/1986 | European Pat. Off. . |
| 0372657 | 6/1990 | European Pat. Off. . |

OTHER PUBLICATIONS

*Tetrahedron Letters,* vol. 33, No. 42, Oct. 13, 1992, Oxford GB, pp. 6283–6286, M.D. Ennis et al., "Enzymatic resolution of 2–Hydroxymethyl–1, 4—benzodioxanes".

*Tetrahedron Letters,* vol. 33, No. 42, Oct. 13, 1992, Oxford GB, pp. 6287–6290, M.D. Ennis et al., "The synthesis of (+) and (−)–Flesinoxan: Application of enzymatic resolution methodology".

*J. Org. Chem,* 1988, 53, pp. 5531–5534, Daniele Bianchi et al., "Anhydrides as Acylating Agents in Lipase–Catalyzed Stereoselective Esterification of Racemic Alcohols".

*Chem. Pharm. Bull.,* 1989, 87(6), pp. 1653–1655, Yoshiyasu Terao et al., "Facile Process for Enzymic Resolution of Racemic Alcohols".

*Drugs of the Future,* 1988, 13, 31–33.

*Agricultural and Biological Chemistry,* vol. 51, No. 5, May 1987, Tokyo, Japan, pp.1265–1270, K. Sakano et al., "Optical resolution of (r,S)–3–Acetoxymethyl–7,8–difluoro–2, 3–dihydro–4H–(1,4)benzoxazine".

*Primary Examiner*—William H. Beisner
*Attorney, Agent, or Firm*—Stevens, Davis, Miller & Mosher, L.L.P.

[57] ABSTRACT

The invention relates to an enzymatic process for the stereoselective preparation of a hetero-bicyclic alcohol enantiomer, characterized in that a substantially pure enantiomer of the general formula

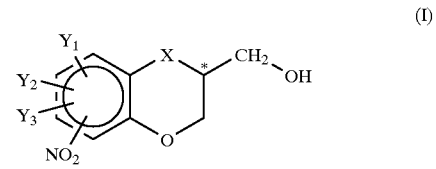

(I)

wherein X is O, S, NH, N—($C_1$–$C_4$)alkyl or $CH_2$;

$Y_1$, $Y_2$ and $Y_3$ are each independently hydrogen or substituents selected from halogen, $C_1$–$C_4$ alkyl, $C_1$–$C_4$ alkoxy, $C_1$–$C_4$ haloalkyl, nitro and cyano;

the $NO_2$ substituent is attached to the bicyclic ring system in the 5- or 7-position; and the C*-atom has either the R or the S configuration;

is prepared from its corresponding alcohol racemate by the following successive reaction steps:

(1) stereoselective esterification,
(2) separation of the alcohol from the ester produced,
(3) hydrolysis of the ester to produce the corresponding alcohol enantiomer, and
(4) conversion of the alcohol enantiomer into the starting racemate under basic conditions in order to allow its reuse.

The invention also relates to a substantially pure alcohol enantiomer of formula I, to the use of the enantiomer for the preparation of a pharmacologically active piperazine derivative, and to substantially pure enantiomeric intermediates.

6 Claims, No Drawings

ENZYMATIC PROCESS FOR THE STEREOSELECTIVE PREPARATION OF A HETERO-BICYCLIC ALCOHOL ENANTIOMER

This application is a divisional application of Ser. No. 08/167,084, filed Dec. 16, 1993.

The present invention relates to an enzymatic process for the stereoselective preparation of a hetero-bicyclic alcohol enantiomer. The invention further relates to a substantially pure alcohol enantiomer and to the use of this enantiomer for the preparation of a pharmacologically active piperazine derivative.

Various biologically active substances, which may be used, for example, in pharmaceutical compositions for human or veterinary application, contain a chiral centre in their molecular structure and therefore give rise to optical isomerism. It is generally known in the art, that often only one of the enantiomers presents the desired optimum biological activity. The presence of the other optical antipode in a composition or agent may cause or invigorate certain side effects and burden the recipient, i.c. the human or animal body. It is generally deemed more and more desirable to administer the biologically active substance in the form of a substantially pure enantiomer, which specifically exhibits the desired biological activity. Therefore, the resolution of a racemate into its enantiomers is often an important step in the preparation process of pharmacologically active substances.

There are essentially three methods available to resolve racemates into their respective enantiomers. The first of these, viz. a resolution based on difference in physical properties, e.g. in crystal structure, is only occasionally applicable.

The second and by far most generally used method of resolution involves a reaction with a—commercially available—optically active reagent to produce diastereomers, which differ in physical properties. So, the diastereomers obtained in this manner can be separated, e.g. by recrystallization, after which the respective enantiomers can be regenerated by a chemical after-treatment. It will be evident, that such a method of resolving racemates is both labour-intensive and expensive, i.a. on account of the use and recovery of an expensive optically active reagent.

Recently, in a more economical method of resolution, enzymes are applied to chemically modify one enantiomer of a racemate selectively, followed by a separation of the modified from the unmodified enantiomer. As an example, Bianchi et al. (J. Org. Chem., 1988, 53, 5531–5534) have reported the use of carboxylic anhydrides as acylating agents in lipase-catalysed selective esterification of racemic alcohols. They have succeeded in obtaining a number of primary and secondary alcohols in high optical purity, viz. with enantiomeric excesses (ee) of over 95%. In fact, for most pharmaceutical applications an enantiomeric excess of at least 95% is required. Although several results obtained by Bianchi and coworkers are promising, with some alcohols no or an insufficient stereoselective conversion was observed. In two recent publications by Ennis et al. (Tetrahedron Lett., 1992, 33, 6283–6286 and 6287–6290), the enzymatic resolution methodology is applied to 2-hydroxymethyl-1,4-benzodioxanes as substrates. The authors have observed, that by using this method of resolution the required standards of optical purity could not be reached, so that a repetition of the enzymatic resolution was necessary.

In order to facilitate the separation of the ester produced from the remaining alcohol, Terao et al. (Chem. Pharm. Bull., 1989, 37, 1653–1655) have used succinic anhydride to produce a succinic monoester enantiomer which could easily be separated from the other, non-reacted alcohol enantiomer by washing with alkaline solution. In this manner the desired active enantiomer could be separated from the undesired inactive enantiomer with less effort, although the results as to optical purity, i.c. the enantiomeric excesses, were generally unsatisfactory. Only with one substrate, viz. (1-hydroxyethyl)benzene, a secondary alcohol, the enzymatic resolution of the racemate by the enantioselective esterification with succinic anhydride was satisfactory.

In addition to the often unpredictable results of the enzymatic resolution of an alcohol racemate, as can be concluded from the above publications, another problem is inherent to the separation of the desired alcohol enantiomer from its corresponding racemate. In fact, each racemate resolution yields in addition to the desired enantiomer the undesired optical antipode, which is generally useless. This means, that at least 50% of the —generally expensive— substrate should be considered as chemical waste, or, in other words, that the yield of the racemate resolution as regards active material is 50% at most. This is clearly illustrated by the Tables in the above Ennis et al. publications, showing that an initial racemate can afford 50% of the desired enantiomer, either in the form of the unconverted alcohol or after conversion to the ester, at most.

It is the objective of the present invention to provide an economically operative process for the stereoselective preparation of a hetero-bicyclic alcohol enantiomer.

This objective can be achieved by an enzymatic process as defined above, which process is characterized according to the present invention, in that a substantially pure enantiomer of the general formula

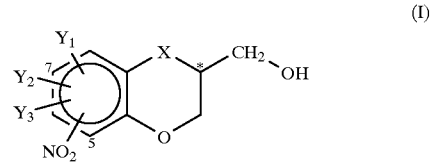

(I)

wherein X is O, S, NH, N-$(C_1-C_4)$alkyl or $CH_2$;
$Y_1$, $Y_2$ and $Y_3$ are each independently hydrogen or substituents selected from halogen, $C_1-C_4$ alkyl, $C_1-C_4$ alkoxy, $C_1-C_4$ haloalkyl, nitro and cyano;
the $NO_2$ substituent is attached to the bicyclic ring system in the 5- or 7-position; and
the C*-atom has either the R or the S configuration;
is prepared from its corresponding alcohol racemate by the following successive reaction steps:
(i) acylation of said racemate with an acylating agent under the influence of an enzyme having a stereoselective esterification activity;
(ii) separation of the unesterified compound from the ester produced, and isolation of the desired substantially pure alcohol enantiomer of formula I or of its ester;
(iii) subjection of the ester produced to a hydrolysis, thus converting said ester into the corresponding alcohol enantiomer; and
(iv) conversion of the undesired alcohol enantiomer into the starting alcohol racemate under basic conditions, in order to allow its reuse.

Completely contrary to expectation, the above basic treatment (step iv) results in racemization of the undesired alcohol enantiomer. This phenomenon cannot be explained, because the proton attached to the chiral centre (C*) is no acidic at all. The alcohol racemate, so obtained, can be reused as a starting material for the next resolution reaction. It will be evident, that this invention makes the enzyme-catalyzed stereoselective preparation of an alcohol enantiomer a feasible process, both from an economical and from an environmental point of view.

Suitable acylating agents for the above acylation reaction are carboxylic anhydrides, as will be exemplified hereinafter, and vinyl esters, such as vinyl acetate, vinyl propionate, vinyl butyrate, vinyl isobutyrate, and the like.

The acylation reaction is preferably carried out in organic solvent systems containing low quantities of water or aqueous buffer.

The enzyme is most often used as a crude solid preparation, which is commercially available, thus facilitating its recovery. Said enzyme, however, may also be applied in an immobilized condition, e.g. covalently bound to or adsorbed on a suitable carrier. The unesterified compound can be separated from the ester produced by using various technics which are known for the separation of related compounds, such as extraction, recrystallization, preparative column chromatography, etc.

A substantially pure alcohol enantiomer, as mentioned above, is to be understood to comprise alcohol compounds with an enantiomeric purity (ee) of over approx. 95%. If in the enzymatic process of the invention such an enantiomeric purity is not reached, the enantiomeric purity can generally be improved up to the desired level by a simple recrystallization procedure. Consequently, isolation of the desired substantially pure alcohol enantiomer, as described hereinbefore, may also include a recrystallization procedure, to improve the enantiomeric purity and to remove minor impurities.

The crucial reaction step, viz. the racemization of the undesired alcohol enantiomer under basic conditions, can easily be carried out both under aprotic and under protic conditions. Suitable bases are sodium hydroxide, potassium hydroxide, lithium hydroxide, ammonium hydroxide, and the like, dissolved in water or in aqueous solvent mixtures comprising water-miscible organic solvents such as alcohols. Examples of bases to be used in aprotic systems are: (a) hydrides, e.g. sodium hydride, in aprotic solvents such as DMSO;(b) potassium alkoxides, such as potassium tert-butoxide and potassium methyl-2-butoxide, in aprotic solvents such as ethers (e.g. THF); and (c) alkyl lithiums and lithium alkyl amides, such as methyl lithium, the various butyl lithiums and lithium diisopropyl amide, also in aprotic solvents, e.g. THF. The alcohol racemate can be recovered in good yields after neutralization with acid, e.g. by extraction with a suitable organic solvent, from the water phase and is then, if desired after evaporation of the solvent, ready for reuse.

The hydrolysis of the ester produced, as mentioned under (iii) above, can conveniently be carried out under acid conditions or under weakly basic conditions to avoid racemization of the alcohol enantiomer to be produced.

As a special embodiment of the present invention, however, the above hydrolysis of the ester and the racemization of the alcohol enantiomer can be combined. In this manner the above reaction steps (iii) and (iv) can be combined so that a reduction with one reaction step can be obtained. Sufficiently strong basic conditions, as defined above for the racemization reaction, are required to perform both functions at the same time, viz. a simultaneous hydrolysis and racemization.

The process of the present invention is preferably intended for the stereoselective preparation of a substantially pure alcohol enantiomer having a benzodioxane structure, so of a compound of the general formula

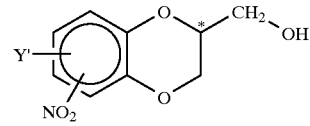

(II)

wherein Y' is hydrogen or a substituent selected from chloro, fluoro and methyl;
the $NO_2$ substituent is attached to the benzodioxane ring in the 5- or 7-position; and
the C*-atom has either the R or the S configuration;
by performing the successive reaction steps as defined hereinbefore.

Preferably the enzyme is applied as a solid and therefore can easily be recovered to allow its reuse. The enzyme recovery is conveniently performed after reaction step (i) above, so after the acylation step has been completed, by using a procedure suitable for this purpose, such as a simple filtration. If an enzyme is used which is bound to a suitable carrier, such as Celite (see the above publication by Bianchi et al.) or glass beads, the enzyme can also be recovered by a simple filtration, if desired followed by washing the filtrate free from impurities.

The use of carboxylic anhydrides is preferred to the application of vinyl esters as acylating agents, because carboxylic anhydrides, such as acetic anhydride, propionic anhydride, butyric anhydride, isobutyric anhydride or hexanoic anhydride, generally have a better performance, in the presence of a suitable enzyme. To facilitate the separation of the unesterified compound from the ester produced, cyclic carboxylic anhydrides are preferred, in particular succinic anhydride or glutaric anhydride. The formed monoester obtained in this manner can easily be separated from the unesterified compound by extraction with a weak alkaline solution under such conditions that the ester remains intact.

Suitable enzymes for performing a stereoselective esterification are hydrolases, such as naturally occurring and engeneered lipases and esterases. Examples of suitable lipases are: *Aspergillus niger, Candida cylindracea* (e.g. Meito® MY 30 or Amano® AY), *Candida lipolytica, Chromobacterium viscosum, Geotrichum candidum, Humicola lanuginosa, Mucor miehei, Mucor javanicus* (e.g. Amano® M), Pig pancreatic lipase, *Penicillium cyclopium, Penicillium roqueforti, Pseudomonas cepacia* (Amano® PS), *Pseudomonas fluorescence* (e.g. Amano® P), *Rhizopus niveus* (e.g. Amano® N), *Rhizopus javanicus* (e.g. Amano® F), *Rhizopus arrhizus* and *Rhizopus delemar*. As opposed to what is suggested in the Bianchi et al. publication, it has now been found, that certain lipases, in particular the lipase *Candida cylindracea*, have a preference for the S enantiomer. Such lipases are therefore capable of stereoselectively esterifying the S enantiomer, as a result of which the remaining R enantiomer can be obtained in a high yield and stereochemical purity. Other lipases, for example *Pseudomonas fluorescence* and many other lipases, prefer the conversion of the R enantiomer and therefore are well suitable for the isolation of the S enantiomer, equally in high yield and stereochemical purity.

The present invention also relates to a substantially pure alcohol enantiomer of the general formula I, presented hereinbefore,
wherein X and the substituents Y have the meanings given above, the substituent NO₂ is attached to the bicyclic ring system in the 5- or 7-position, and the C*-atom has the R configuration.

This enantiomer can conveniently be obtained by using the enzymatic process of the invention. This enantiomer can be used as a key intermediate in the process for preparing certain pharmacologically active piperazine derivatives as will be explained hereinafter.

In Drugs of the Future 1988, 13, 31–33, the synthesis of flesinoxan hydrochloride, a potent orally-active 5-HT$_{1A}$ agonist, is described. The racemic benzodioxan, corresponding with the above formula II, wherein Y' is a 7-chloro substituent, is first converted with benzoyl chloride to protect its alcohol function. Then catalytic hydrogenation followed by a reaction with bis(chloroethyl)amine results in a racemic piperazine compound. In this phase the resolution of the piperazine racemate is carried out with (+)-camphorsulphonic acid. After several recrystallizations, the optically pure R-(+)-enantiomer is obtained. Reaction of this enantiomer with N-(4-fluorobenzoyl)aziridine, deprotection of the hydroxy group by saponification of the benzoate ester, and finally treatment with hydrochloric acid yields the desired substantially pure (+)-enantiomer, viz. flesinoxan.HCl. In the above-mentioned recent publication by Ennis et al. (Tetrahedron Lett., 1992, 33, 6287–6290), the enzymatic resolution of flesinoxan and its optical antipode, so a final stage resolution, is described. After a laborious double-pass enzymatic process, the desired flesinoxan could be isolated in a satisfactory enantiomeric purity.

It will be obvious from the above, that the described flesinoxan preparation is laborious and expensive, in particular because of the laborious resolution of the racemate in a so advanced stage of the multi-step synthetic process. It will be obvious, that inevitable losses of active material during resolution are the more detrimental in an advanced stage of the synthetic process.

It has now been found, that the substantially pure alcohol enantiomer of the general formula I can conveniently be used as a key intermediate in the synthesis of pharmacologically active piperazine derivatives, because a laborious resolution of the racemate in an advanced stage of the multistep synthesis is avoided.

Consequently the present invention also relates to the use of a substantially pure alcohol enantiomer of the general formula I, presented hereinbefore, wherein X and the substituents Y have the meanings given above, the NO₂ substituent is attached to the bicyclic ring system in the 5-position, and the C*-atom has the R configuration, for the preparation of a pharmacologically active piperazine derivative, by subjecting said enantiomer to the following reaction sequence:

(i) protection of the free hydroxy group by a suitable hydroxy-protecting group, while retaining the absolute configuration of the C*-atom, to produce a compound of the general formula

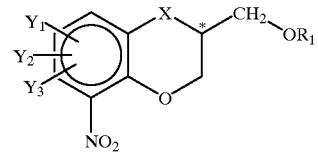

(III)

wherein R₁ is a hydroxy-protecting group;

(ii) reduction of the nitro substituent, in order to convert said substantially pure enantiomer of formula III into an amine compound of the general formula

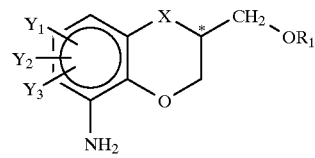

(IV)

while retaining the absolute configuration of the C*-atom;

(iii) conversion of the above-obtained amino compound of formula IV into a piperazine compound of the general formula

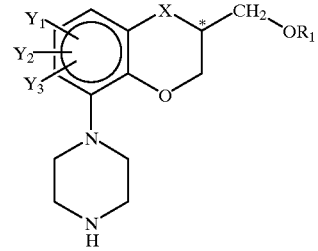

(V)

while retaining the absolute configuration of the C*-atom;

(iv) derivatizing said piperazine compound of formula V, while retaining the absolute configuration of the C*-atom, to a piperazine derivative of the general formula

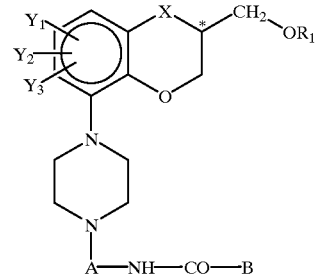

(VI)

wherein A is a straight or branched C₂–C₄ alkylene group, and

B is a phenyl group or a heterocyclic group, selected from thienyl, pyranyl, furyl, pyrrolyl, pyridyl and pyrazinyl, which groups may be substituted with one or more substituents selected from halogen, C₁–C₃ alkyl, C₁–C₃ haloalkyl, cyano, nitro, hydroxy, esterified hydroxy and C₁–C₃ alkoxy, by reacting said piperazine compound of formula V, either
   (a) with a compound of the general formula

# (VII)
L—A—NH—CO—B wherein L is a leaving group, preferably selected from chloro, mesylate, and tosylate, or
   (b) with a compound of the general formula

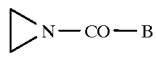 (VIII)

producing a piperazine derivative of the general formula VI wherein A is ethylene; and finally
(v) deprotection of said compound of formula VI to the free alcohol enantiomer of the general formula

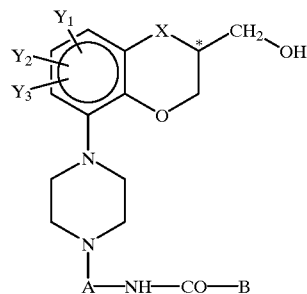 (IX)

wherein the C*-atom has the R-configuration.

As will be clear from the above, the above subsequent reaction steps can easily be performed under retention of the absolute configuration of the C*-atom, so that the enantiomeric purity of the final piperazine derivative is not compromised.

The free hydroxy group can be protected (reaction step i) by a suitable ester or ether function. Examples of suitable hydroxy-protecting groups are: (trihydrocarbyl)silyl, (dihydrocarbyl) (hydrocarbyloxy)silyl, tert. $(C_4-C_{12})$alkyl, (opt. substituted)phenoxy[$(C_2-C_8)$dialkyl]ethyl, $(C_1-C_4)$ alkoxy[$(C_2-C_8)$dialkyl]methyl, (thio)acetal-constituting groups such as di- and tetrahydropyran-2-yl and di- and tetrahydrofur-2-yl, and ester-constituting groups derived from mono-, di- or tri-substituted acetic acid, wherein the substituents are preferably selected from $(C_1-C_{12})$alkyl and optionally with one or more substituents substituted phenyl, optionally with one or more methyl substituted cyclohexanecarboxylic acid or adamantane carboxylic acid. The above term hydrocarbyl includes $(C_1-C_8)$alkyl, $(C_2-C_8)$ alkenyl, $(C_2-C_8)$alkynyl, phenyl and phenyl substituted with one or more substuents. Suitable substituents for the above phenyl and phenoxy groups are: hydroxy, alkoxy, alkylcarbonyloxy, amino, alkylamino, dialkylamino, alkylcarbonylamino, alkylsulphonylamino, nitro, alkylsulphonyl, alkylcarbonyl, halogen, cyano, alkyl, the alkyl substituents of which comprise 1 to 5 carbon atoms, and $(C_5-C_{12})$cycloalkyl.

The reduction of the nitro group to the amino group (step ii) can conveniently be carried out with hydrogen under the influence of a suitable metal-catalyst, e.g. Pd/C, in a suitable polar organic solvent, e.g. an alcohol.

The conversion of the amino compound into the piperazine compound (step iii) can easily be carried out, for example with the aid of bis(2-chloroethyl)amine, in a suitable organic solvent, e.g. an aromatic hydrocarbon such as toluene, chlorobenzene, and the like.

The reaction step defined under (iv) above is preferably be carried out as described in European patent specification 138280, viz. in an inert organic solvent or without a solvent, and under the reaction conditions as described in said patent specification.

The final deprotection of the hydroxy group can be carried out with agents suitable for the ester or ether fission. Esters can conveniently be hydrolyzed, under weakly alkaline or under acidic conditions, under conservation of the absolute configuration of the C*-atom. The ether fission is preferably carried out with the aid of strong acids in organic solvents.

The present invention further relates to new intermediates in the above reaction sequence, viz. to a substantially pure enantiomer of the general formula III and IV, presented hereinbefore,
wherein X and the substituents Y have the meanings given above, and
   the configuration of the C*-atom corresponds with the R configuration of the C*-atom of the above-mentioned formula I compound.

The invention finally relates to a method of preparing a substantially pure piperazine derivative enantiomer of the general formula IX, presented above, by first preparing the substantially pure alcohol enantiomer of the general formula I, presented hereinbefore, wherein the C*-atom has the R configuration, from its corresponding alcohol racemate by performing the successive reaction steps as defined hereinbefore, followed by conversion of said formula I compound into the desired piperazine derivative via the reaction sequence as defined above.

The invention will now be described in greater detail with reference to the following specific examples.

EXAMPLE I

A solution of 125 mM (±)-2,3-dihydro-5-nitro-7-chloro-1,4-benzodioxan-2-methanol (BDA), 250 mM propionic anhydride and 0.2% (w/v) lipase *Pseudomonas fluorescens* (Amano® P) in TBME (tert-butyl methyl ether)/hexane/water(50/50/0.1 v/v/v) is incubated at 37° C. while stirring. After 80% conversion (esterification of the alcohol), the reaction is stopped by filtering off the alcohol are produced ester and remaining alcohol are separated on a Zorbax® C-8 column. The enantiomeric excess of the remaining alcohol is analyzed using a chiral α-glycoprotein (AGP) column. The enantiomeric excess of the remaining alcohol and produced ester is also determined by $^1$H-NMR without separation, using (+)- or (−)-trifluoromethyl-9-anthracenemethanol chiral resolving agent. The remaining alcohol contains the S-(−)-alcohol with an enantiomeric excess of 97.5%.

EXAMPLE II

In a corresponding manner as described in Example I the esterification is performed with 0.2% (w/v) lipase *Candida cylindracea* (Meito® MY). After conversion of 69% alcohol, the reaction is stopped. The remaining alcohol contains R-(+)-alcohol with an enantiomeric excess of 97.5%. The R-(+)-alcohol is characterized by its $^1$H-NMR spectrum, as described in Example I. The specific rotation of R-(+)-BDA in acetonitrile is determined: $[\alpha]_D^{25}=+181.1°$.

In a corresponding manner R-(+)-2,3-dihydro-5-nitro-7-methyl-1,4-benzodioxan-2-methanol and R-(+)-2,3-dihydro-5-nitro-1,4-benzodioxan-2-methanol are prepared, equally with high enantiomeric excesses.

EXAMPLE III

A solution of 250 mM (±)-BDA, 500 mM butyric anhydride and 0.5% (w/v) lipase *Candida cylindracea* (Meito® MY) in hexane/ethyl acetate/water (50/50/0.2 v/v/v) is incubated at 25° C. while stirring. After conversion of 65% alcohol, the reaction is stopped. The remaining alcohol contains the R-(+)-alcohol with an enantiomeric excess of 97.5%.

EXAMPLE IV

In a corresponding manner as described in Example III, 250 mM (±)-BDA is incubated with 500 mM isobutyric resp. hexanoic anhydride. After conversion of 63 resp. 60% alcohol, the reaction is stopped. The remaining alcohol contains the R-(+)-alcohol, in both cases with an enantiomeric excess of 97.5%.

EXAMPLE V

A solution of 350 mM (±)-BDA, 600 mM succinic anhydride and 2.4% (w/v) lipase *Candida cylindracea* (Meito® MY) in TBME/acetonitrile/water (90/10/0.6 v/v/v) is incubated at room temperature while stirring. After conversion of 70% alcohol, the reaction is stopped by filtration. The remaining alcohol contains the R-(+)-enantiomer with an enantiomeric excess of 98%.

EXAMPLE VI
Enantioselective esterification

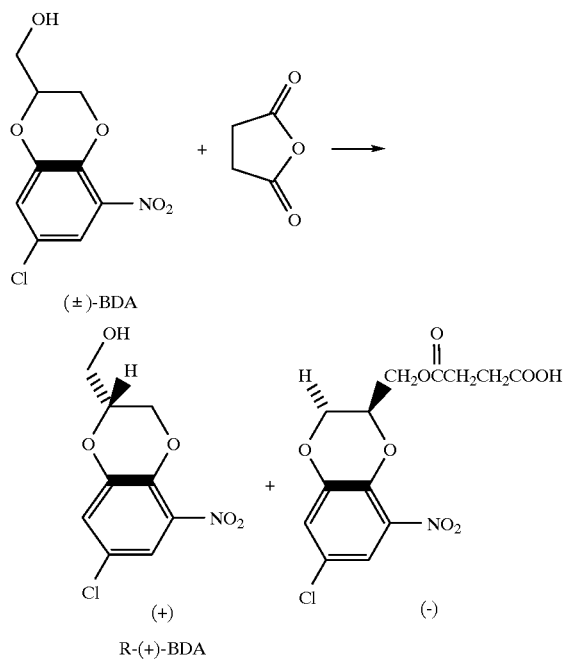

A solution of 15.2 kg (±)-BDA, 7.6 kg succinic anhydride and 3.7 kg lipase *Candida cylidracea* (Meito® MY) in a mixture of 200 l tert-butyl methyl ether (MTBE), 17.5 l acetonitrile and 925 ml water is incubated under nitrogen at room temperature in a rection vessel. After a conversion has been reached of 60–63% (HPLC, approx. 20 h), the reaction is stopped by filtering off the enzyme. The enzyme is washed twice with 10 l MTBE, and the organic layer is washed successively with 90 l and 30 l aqueous carbonate (150 g $Na_2CO_3$ in 1 l water). The carbonate solution is extracted twice with 10 l MTBE. Then the combined organic layers are successively washed with 30 l water, with dil. hydrochloric acid obtained by dissolving 40 ml 36% HCl in 15 l water, and with 10 l water. The MTBE is distilled off in vacuo at 60° C. The crystalline residue (4.6 kg) is dissolved in 15 l 96% EtOH at 60° C.; to this solution are added 10 l n-hexane while stirring. The mixture is cooled to approx. 10° C., and after 2 to 10 h stirring the crystalline material is sucked off, washed successively with 10 l EtOH/hexane (15/35 v/v) and with 5 l n-hexane, and dried. The crystalline material is the pure (ee98%) (+)-enantiomer, viz. R-(+)-2,3-dihydro-5-nitro-7-chloro-1,4-benzodioxan-2-methanol [R-(=)-BDA]; yield approx. 4 kg.

Melting point 116.0° C.; $[\alpha]_D^{25}=+194.8°(c=4.5;CH_3OH)$.

EXAMPLE VII

Saponification of the S-(–)-BDA ester produced.

Reaction equation:

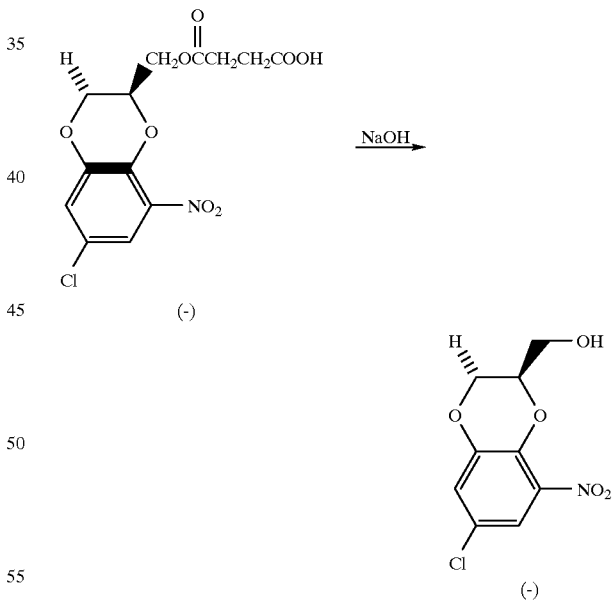

To the combined aqueous layers from the experiment of Example VI are added 15 l 50% NaOH at approx. 23° C. The reaction mixture is stirred for approx. 15 h at 23° C. and is then cooled to 5° C. After grafting, the mixture is stirred for 3 h at 5° C. The crystalline material is sucked off, washed with 60 l water and dried. The resulting alcohol, having an excess of the S-(–)-BDA enantiomer, is obtained in a yield of approx. 10 kg.

EXAMPLE VIII
Racemization of the S-(−)-BDA enantiomer.

Reaction equation:

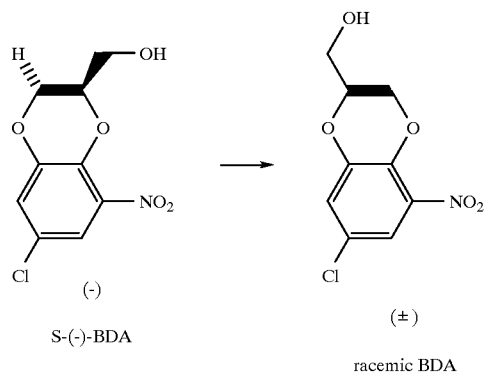

S-(−)-BDA, obtained according to Example VII, in a quantity of 1 kg, is dissolved in 6 l n-propanol under nitrogen and reflux. To this solution are added 235 ml 2N aqueous NaOH in approx. 15 min. The solution is allowed to reflux for 1.5 h. After cooling to approx. 40° C., 47 ml conc. HCl-solution are added (to pH=3). The propanol is distilled off in vacuo at approx. 60° C. To the residue are added 4 l n-hexane, and the solution is grafted, while cooling to 20° C. and slowly stirring. After stirring for two hours at 20° C. and overnight at 0° C., the crystalline material is sucked off and washed twice with 0.5 l n-hexane. The crystalline material is then stirred with 7.5 l water on approx. 70° C. for 1 hour. After cooling to 20° C., adding 350 ml n-hexane and stirring for another hour, the crystalline material is filtered off and washed twice with 0.5 l n-hexane. After drying, the desired racemic BDA is obtained in a yield of 850 g; content 95%; ee=0. Melting point 108.2° C.

The racemization proceeds equally successful with the aid of lithium diisopropyl amide as the base in THF as the solvent: reaction temperature 40° C.; complete racemization after 5.5 hours.

EXAMPLE IX
Saponification and simultaneous racemization of the S-(−)-BDA ester To an aliquot, which obtained 43.5 g (126 mmol) S-(−)-BDA ester, 620 ml aqueous carbonate (150 g $Na_2CO_3$ in 1 l water), 150 ml water and 59 ml acetonitrile, of the basic water layer obtained as in example VI 250 ml ethanol and 50 ml 50% w/v aqueous sodium hydroxide solution is added. The reaction mixture is stirred under reflux for 16 h. After cooling down to 40° C. 160 ml 12 n aqueous hydrochloric acid solution is carefully added (pH is approximately 5). The reaction mixture is cooled down to room temperature after which the solid material is sucked off, washed with water and dried. 23.8 light brown (±)-BDA with an enantiomeric excess of 0 is obtained.

EXAMPLE X
Preparation of flesinoxan from R-(+)-BDA

Reaction equations:

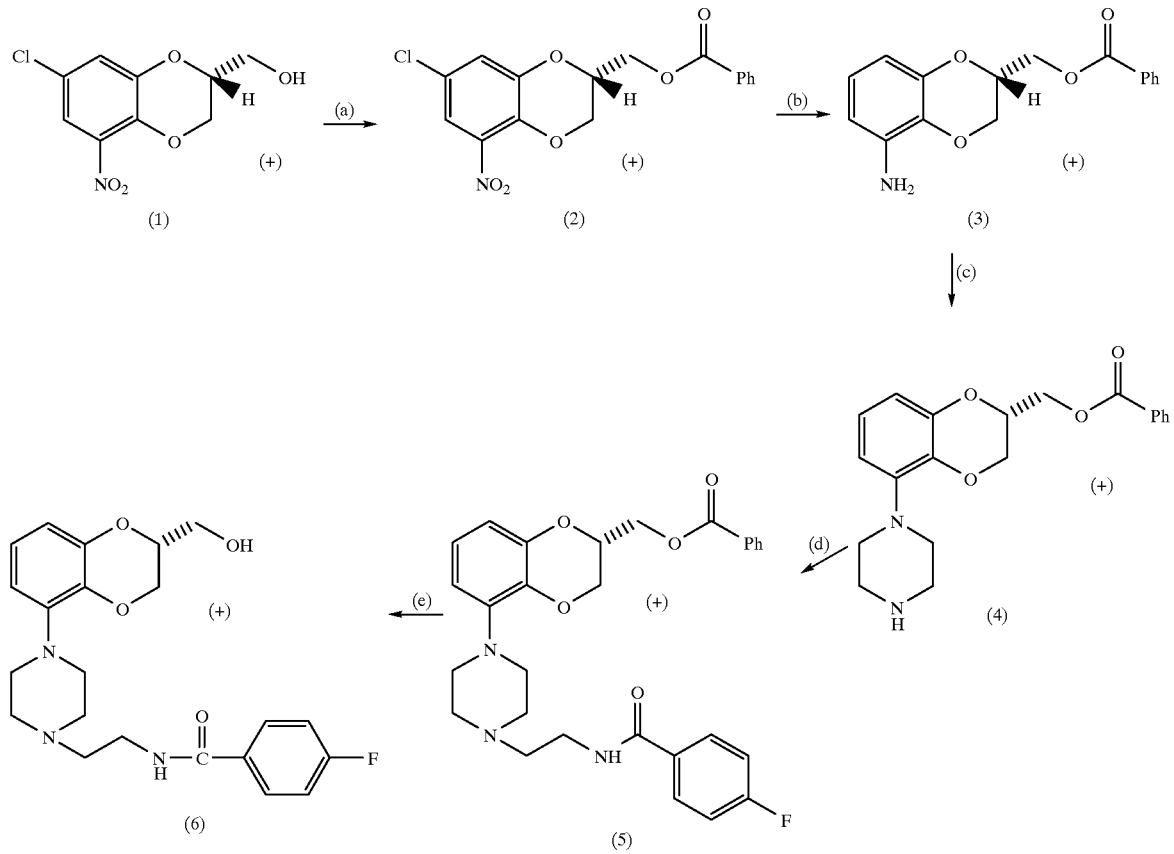

(a). Benzoylation of R-(+)-BDA(1) with benzoyl chloride in methylene chloride as the solvent, to produce compound (2).

To a solution of 20 g (0.081 mol) compound (1) in 250 ml dichloromethane and 12 ml triethylamine is added dropwise 10.1 ml (0.086 mol) benzoylchloride; temp. 25° C. After addition of 10 ml water and stirring for 10 min the layers are separated. The organic layer is washed with 50 ml water and the combined water layers are extracted with 25 ml dichloromethane. The organic layers are combined and evaporated at 100 mbar and 30° C. After addition of 100 ml toluene, the product is evaporated to dryness (10 mbar, 50° C.).

The desired compound (2) is obtained in a yield of 97.3%; purity 97.5%. TLC (eluens: $CH_2Cl_2/CH_3OH/NH_4OH=94/5/1$): Rf=0.71.

(b). Reduction of the nitro-compound (2) to the corresponding amino-compound (3) with hydrogen in the presence of a catalytic amount of Pd/C; EtOH as the solvent.

To a solution of 6.0 g (16.7 mmol) compound (2) in 120 ml ethanol and 40 ml ethyl acetate is added 1.50 g Pd/C preparation (39.1% Pd/C 10% and 60.9% water). After stirring for 5 min, 10.8 g (10 eq) ammonium formiate is added and the mixture is stirred, at first 1 hour at ambient temp. and then 2 hours at 40° C. The reaction mixture is cooled to 20–25° C., and the Pd/C is filtered off and washed with 50 ml ethanol. The ethanol is evaporated at 100 mbar and 50° C. The residue is dissolved in 75 ml ethyl acetate and 15 ml 2N aqueous sodium hydrode solution. After separation of the layers, the water layer is extracted twice with 10 ml ethyl acetate, the combined organic layers are washed twice with 25 ml water and reduced to dryness at 100 mbar and 50° C. After drying in vacuo at 50° C., the desired product (3), having a purity of 96.0%, is obtained in a yield of 97.0%.

TLC (see above): Rf=0.67. Melting point of the HCl-salt: 218–223° C. $[\alpha]_D^{25}=+65.1°$ (c=3.38; $CH_3OH$).

(c). Conversion of the amino-compound (3) to the corresponding piperazine-compound (4) with bis(2-chloroethyl)amine.HCl in xylene as the solvent.

To a solution of 4.40 g (14.8 mmol) compound (3) in 50 ml xylene is added 2.8 g (14.8 mmol) bis(2-chloroethyl)amine.HCl. The reaction mixture is refluxed for 48 hours under nitrogen. After cooling the reaction mixture to 35° C., 1.36 ml 50% aqueous NaOH-solution in 25 ml 5% aqueous $NaHCO_3$-solution is added. The reaction mixture is stirred at 35° C. for 3 hours, after which 10 ml 2N aqueous NaOH-solution and 20 ml water are added. After stirring at 35° C. for 10 min, the reaction mixture is cooled to 20–25° C. and the layers are separated. The xylene layer is washed three times with 25 ml water. The organic layer is reduced to dryness (100% ethanol as entrainer) at 10 mbar and 50° C. The desired product (4), having a purity of 85.5%, is obtained in a yield of 82.3%.

TLC (see above): Rf=0.07. Melting point of the HCl-salt: 183–186° C. $[\alpha]_D^{25}=+63.66°$ (c=1.67; $CH_3OH$).

(d). Reaction of the piperazine-compound (4) with 4-fluorobenzoylaziridine to produce compound (5).

p-Fluorobenzoylaziridine (53.8 g; 325 mmol) and 200 ml toluene are added to 100.7 g (284 mmol) of compound (4). The reaction mixture is kept under reduced pressure at 80° C. (rotorvapor); 150 ml is evaporated. After addition of 100 ml toluene the reaction mixture is treated as described above for another 2 hours. After evaporation to dryness, methanol is added to the residue and the product is allowed to crystallize at 5° C. The product is sucked off, washed with methanol (200 ml) and hexane (400ml) successively, and dried. The desired compound 5, having a purity of 82% is obtained in a yield of 105 g (71%). Work-up of the mother liquor results in an additional quantity of desired product.

TLC (see above): Rf=0.59. Melting point: 126–127° C. $[\alpha]_D^{25}=+56°$. (c=4.32; $CH_3OH$).

(e). Saponification of the ester (5) with KOH in EtOH, followed by acidification with HCl in EtOH, to produce flesinoxan (6).

To a suspension of 104 g (0.2 mol) of compound (5) in 1500 ml 96% ethanol is added a solution of 14 g (0.25 mol) KOH in 10 ml water. After stirring at 20–25° C. for 3.5 hours, the ethanol is evaporated at 100 mbar and 50° C. Water (500 ml) and dichloromethane (200 ml) are added to the residue and the reaction mixture is stirred for 5 min. After separation of the layers, the water layer is extracted with 250 ml dichloromethane. The combined organic layers are washed twice with 100 ml water. After drying, the organic solution is evaporated to a residual volume of approx. 200 ml. To this residue is added 300 ml ethyl acetate, and 100 ml of liquid is evaporated. After addition of 100 ml n-hexane, the product is allowed to crystallize overnight at 5° C. The crystalline product is filtered, washed successively with 30 ml cold ethyl acetate and 200 ml n-hexane, and dried at 30° C. Flesinoxan (purity 78%) is obtained in a yield of 73 g.

TLC (see above): Rf=0.67. Melting point: 183–185° C. $[\alpha]_D^{20}=+27.8°$(c=2.49; $CH_3OH$).

EXAMPLE XI

A solution of 0.2 M 5-chloro-2,3-dihydro-7-nitro-1,4-benzodioxin-2-methanol, 0.34M succinic anhydride and 2% (w/v) lipase *Candida cylindracea* (Meito® MY) in TBME/acetonitril/water (90/10/0.3 v/v/v) is incubated at room-temperature while stirring. After conversion of 41% alcohol (determined by use of a Zorbax C-8 column), the reaction is stopped by filtration. The remaining alcohol contains the (+)-enantiomer with an enantiomeric excess of 38% (determined by use of a Chiracel®-OD column).

EXAMPLE XII

Preparation of 6-chloro-2,3-dihydro-8-nitro-1,4-benzoxazine-3-methanol

Reaction scheme:

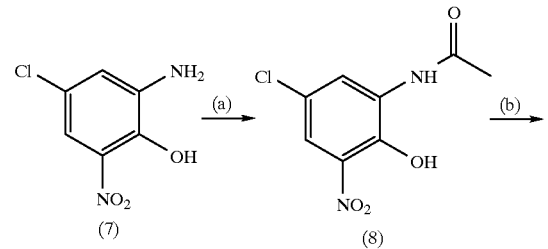

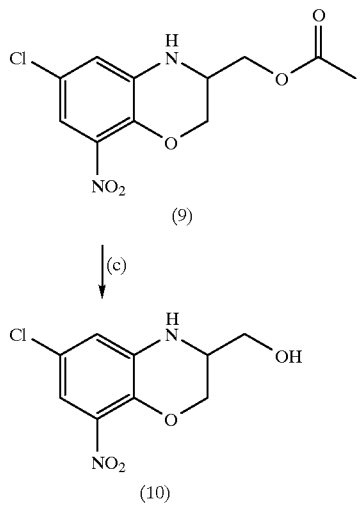

(a) To a suspension of 18.5 g (91 mmol) compound (7) in 50 ml toluene 30 ml (314 mmol) acetic anhydride is added under stirring.

After 4 h heating at 100° C. another 10 ml acetic anhydride is added. Heating is continued for an other 2 h. After removal of the heating bath about 25 ml ethanol is added carefully. After cooling down to room-temperature the reaction mixture is worked up with ethylacetate and water. The organic layer is washed twice with water and dried on magnesiumsulfate. After filtration the solvent is evaporated under vacuum. To 18.23 g of the light brown solid 75 ml ethanol and 80 ml of a 2 n aqueous sodium hydroxide solution is added. The dark red suspension is stirred during the night at room-temperature. After cooling down to 0° C. 90 ml 2 n aqeous hydrochloric acid solution is added. The solid material is sucked off and washed twice with water. After drying at room-temparature and normal pressure 16.5 g orange powder (8) is obtained.

TLC (eluens: ethylacetate/petr. ether 40–65° C.=50/50): Rf=0.3. Melting point: 156–160° C.

(b) To a solution of 8 g (34.5 mmol) compound (8) in a mixture of 80 ml toluene and 80 ml 1-methyl-2-pyrrolidone 5.6 g (40 mmol) powdered potassium carbonate is added. The reaction mixture is stirred at reflux temperature during one hour and water is removed by means of a Dean-Stark apparatus. Toluene is distilled off at atmospheric pressure. After cooling down to 100° C. 9.3 g (41 mmol) glycidyl tosylate is added. After stirring at 120° C. during 4.5 h the suspension is cooled down to room-temperature. The reaction mixture is diluted with water and ethylacetate and brought on pH 5 with a 2 n aqueous hydrochloric acid solution. The water layer is extracted twice with ethylacetate. The combined organic layers are washed with brine and dried on magnesium sulfate. After filtration of the magnesium sulfate and evaporation of the solvent under vacuum 10.86 g dark brown oil is obtained. Purification by medium pressure chromatography (eluens: ethylacetate/petr. ether 40–65° C.=25/75) gives 4.18 g compound (9) as red plates. Melting point: 76–84° C. TLC (see above): Rf=0.15.

(c) To a suspension of 3 g (10 mmol) compound (9) in a mixture of 100 ml methanol and 30 ml water 1.44 g powdered potassium carbonate is added. After stirring at room-temperature for 1.5 h the reaction mixture is worked up by dilution with water and two times extraction with ethylacetate. The combined organic layers are washed three times with diluted brine and dried on magnesium sulfate. After filtration of the magnesium sulfate and evaporation of the solvent under vacuum 2.53 g compound (10) (NMR) is obtained as orange solid material.

TLC (ethylacetate/petrol ether 40–65° C. =75/25): Rf=0.3.

$^1$H-NMR: δ (ppm) 6.99 (d, 1H, arom); 6.90 (s, 1H, NH); 6.88 (d, 1H, arom); 5.02 (t, 1H, CH$_2$OH); 4.19 (dd, 1H, OCH$_2$CH); 4.11 (dd, 1H, OCH$_2$CH); 3.40/3.50 (cluster, 3H, CHCH$_2$OH).

EXAMPLE XIII

A solution of 0.35 M 6-chloro-2,3-dihydro-8-nitro-1,4-benzoxazine-3-methanol, 0.6 M succinic anhydride and 3.3% (w/v) lipase *Candida cylindracea* (Meito® MY) in TBME/acetonitril/water (90/10/0.6 v/v/v) is incubated at room-temperature while stirring. After conversion of 47% alcohol (determined by use of a Zorbax C-8 column), the reaction is stopped by filtration. The remaining alcohol contains the (+)-enantiomer with an enantiomeric excess of 39% (determined by use of a Chiracel®-OD column).

EXAMPLE XIV

A solution of 0.13 M 2,3-dihydro-7-nitro-1,4-benzodioxin-2-methanol, 0.24 M butyric anhydride and 25% (w/v) lipase in diisopropylether/acetonitril/water (50/50/0.5 v/v/v) is incubated at room-temperature while stirring. After conversion of 64% alcohol, the reaction is stopped by filtration. The remaining alcohol contains the (+)-enantiomer with an enantiomeric excess of 42.4%.

EXAMPLE XV

Racemisation of (+)-2,3-dihydro-7-nitro-1,4-benzodioxin-2-methanol

To a solution of 0.1 g (47 mmol) (+)-2,3-dihydro-7-nitro-1,4-benzodioxin-2-methanol ($[α]_D^{20}$=+65.5 (c=0.58, 96% ethanol) in 15 ml ethanol 0.2 ml (40 mmol) of a 2 n aqueous sodium hydroxide solution is added. After reflux during 125 h the reaction mixture is cooled down to room-temperature. The reaction mixture is diluted with water and extracted twice with ethylacetate. The organic layer is dried on magnesium sulfate. After filtration of the magnesiumm sulfate and evaporation of the solvent under vacuum 0.1 g light brown solid material is obtained. The specific rotation (see above) is 0. Analysis of the enantiomeric excess by using a chiral α-glycoprotein (AGP) column results in an ee=0.

Using n-propanol as the solvent results in a 30 h reaction time.

EXAMPLE XVI

Racemisation of (+)-5-chloro-2,3-dihydro-7-nitro-1,4-benzodioxin-2-methanol

To a solution of 0.85g (3.46 mmol) (+)-5-chloro-2,3-dihydro-7-nitro-1,4-benzodioxin-2-methanol ($[α]_D^{20}$=+55 (c=0.4, ethanol)) in 80 ml ethanol 15 ml of a 2 n aqueous sodium hydroxide solution is added. After reflux for 16 h the mixture is cooled down to room-temperature and worked up as described in example XV. The specific rotation (see above) of the obtained solid material is 0. Chiral analysis on a chiracel-OD column showes an ee=0.

EXAMPLE XVII

Racemisation of (+)-6-chloro-2,3-dihydro-8-nitro-1,4-benzoxazine-3-methanol

To a solution of 2 g (8.18 mmol) (+)-6-chloro-2,3-dihydr-8-nitro-1,4-benzoxazine-3-methanol ($[α]_D^{20}$=+14 (c=0.71, 96% ethanol)) in 50 ml ethanol a 2 n aqueous sodium hydroxide solution is added. After 3 h reflux an other aliquot of 1 ml of a 2 n aqueous sodium hydroxide solution is added. After reflux for 32 h the reaction mixture is cooled down to room-temperature and diluted with brine. The water layer is extracted twice with ethylacetate.

The combined organic layers are washed twice with diluted brine and dried on magnesium sulfate. After filtration of the magnesium sulfate and evaporation of the solvent in vacuum there is obtained 1.83 g orange brown solid material. The specific rotation is 0 and chiral analysis on a chiracel-OD column showed an ee=0.

EXAMPLE XVIII

Racemisation with the aid of sodiumhydride

To a mixture of 0.2 g (0.8 mmol) R-(+)-BDA and 0.01 g (0.5 equivalent) of a 60% sodium hydride suspension in mineral oil 5 ml DMF is added. After termination of gas development the orange solution is stirred at room-temperature. The racemisation was complete within 0.75 h as analysed with the aid of a Chiracel-OD column.

In THF as the solvent, the reaction proceeds equally sucessfull.

We claim:

1. An enzymatic process for the stereoselective preparation of a hetero-bicyclic alcohol enantiomer of the formula

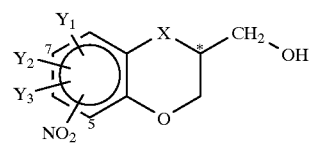

(I)

wherein X is O, S, NH, N—($C_1$–$C_4$)alkyl or $CH_2$;

$Y_1$, $Y_2$ and $Y_3$ are each independently hydrogen or substituents selected from halogen, $C_1$–$C_4$ alkyl, $C_1$–$C_4$ alkoxy, $C_1$–$C_4$ haloalkyl, nitro and cyano;

the $NO_2$ substituent is attached to the bicyclic ring system in the 5- or 7-position; and the C*-atom has either the R or the S configuration;

from its corresponding alcohol racemate by a process comprising the following successive reaction steps:

(i) acylating said racemate with an acylating agent under the influence of an enzyme having a stereoselective esterification acitivity;

(ii) separating the unesterified compound from the ester produced, and isolating the desired substantially pure alcohol enantiomer of formula I or of its ester;

(iii) subjecting of the ester produced to a hydrolysis, thus converting said ester into the corresponding alcohol enantiomer, and preparing said alcohol enantiomer in an enantiomeric purity (ee) of over 95% by (iv) converting of the undesired alcohol enantiomer into the starting alcohol racemate under basic conditions, in order to allow its reuse.

2. A process as claimed in claim 1, characterized in that reaction steps (iii) and (iv) are combined by using sufficiently strong basic conditions to perform the simultaneous hydrolysis of the ester and racemization of the alcohol enantiomer.

3. A process as claimed in claim 1, characterized in that a substantially pure enantiomer of the formula

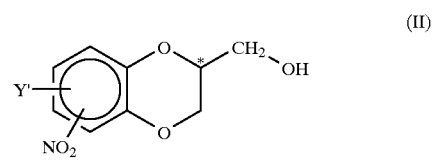

(II)

wherein Y' is hydrogen or a substituent selected from chloro, fluoro and methyl;

the $NO_2$ substituent is attached to the bicyclic ring system in the 5- or 7-position; and the C*-atom has either the R or the S configuration;

is prepared by the successive reaction steps as defined in claim 1.

4. A process as claimed in claim 1 or 2, characterized in that a carboxylic anhydride is used as the acylating agent.

5. A process as claimed in claim 4, characterized in that succinic anhydride or glutaric anhydride is used as the acylating agent.

6. A process as claimed in claim 1 or 2, characterized in that a lipase or esterase having a stereoselective esterification activity is used as the enzyme.

* * * * *